United States Patent [19]

Hackenberger et al.

[11] Patent Number: 4,506,089

[45] Date of Patent: Mar. 19, 1985

[54] PREPARATION OF METHYL M-NITROBENZOATE

[75] Inventors: Alfred Hackenberger, Ludwigshafen; Manfred Patsch, Wachenheim; Manfred Gaeng, Bobenheim-Roxheim, all of Fed. Rep. of Germany

[73] Assignee: BASF Aktiengesellschaft, Ludwigshafen, Fed. Rep. of Germany

[21] Appl. No.: 586,668

[22] Filed: Mar. 6, 1984

[30] Foreign Application Priority Data

Mar. 10, 1983 [DE] Fed. Rep. of Germany ....... 3308460

[51] Int. Cl.$^3$ ...................... C07C 76/06; C07C 79/46
[52] U.S. Cl. .................................................. 560/020
[58] Field of Search .......................................... 560/20

[56] References Cited

U.S. PATENT DOCUMENTS 2,314,212  3/1943  Hennion ............................ 560/20 X

OTHER PUBLICATIONS

Houben–Weyl, Methoden der Organischen Chemie, vol. 10/1, p. 620.
Org. Syntheses, Coll., vol. I, (1932), pp. 372–374.
Ullmanns Encyklopädie der Technischen Chemie, vol. 10, pp. 455–464.

Primary Examiner—Bernard Helfin
Attorney, Agent, or Firm—John H. Shurtleff

[57] ABSTRACT

Methyl m-nitrobenzoate is prepared by a process in which an isomer mixture is treated with from 10 to 1000% by weight of water in the presence of from 0.05 to 20% by weight of an emulsifier, the percentages being based on the weight of the isomer mixture,
(a) in a first stage at from 55° to 100° C. and a pH from 2 to 8 and then
(b) in a second stage at from 10° to 40° C. and a pH of not less than 9.

The methyl m-nitrobenzoate obtainable by the process of the invention is a useful starting material for the preparation of dyes and crop protection agents.

12 Claims, No Drawings

PREPARATION OF METHYL M-NITROBENZOATE

The present invention relates to a process for the preparation of methyl m-nitrobenzoate by treating an isomer mixture with from 10 to 1000% by weight of water in the presence of from 0.05 to 20% by weight of an emulsifier, the percentages being based on the weight of the isomer mixture, (a) in a first stage at from 55° to 100° C. and a pH from 2 to 8, and then (b) in a second stage at from 10° to 40° C. and a pH of not less than 9.

It is known (Houben-Weyl, Methoden der organischen Chemie, Volume 10/1, page 620) that the nitration of benzoates gives a mixture of the three possible isomers. The mixture is said to contain 72.6% (nitration with nitric acid at 25° C.) or 81-85% (action of nitrating acid at 5°-15° C. on the ester dissolved in H₂SO₄) of methyl m-nitrobenzoate. The last-mentioned procedure (Org. Synth., Coll, Vol. I, 372-374 (N.Y. 1948) gives an isomer mixture which contains a high proportion of the desired m-isomer. After the reaction, the mixture is poured onto ice, and the product is filtered off under suction. The residue from filtration is washed with water and treated with ice-cold methanol in order to remove the o-ester and other impurities. The mixture is then filtered under suction once again, and the residue is washed with cold methanol and dried.

However, it is not possible to obtain the pure m-nitro ester by the processes described. When the nitration mixture is introduced into water, a mixture of the three isomeric methyl nitrobenzoates is obtained; this mixture contains about 10% of the o-isomer and as much as 2% of the p-isomer.

Furthermore, the isomer mixture contains small amounts of methyl dinitrobenzoate, nitrophenol compounds and other unknown by-products, which may be present in varying amounts. To purify the desired 3-nitro compound, the above-mentioned additional recrystallization from an organic solvent, eg. methanol, must therefore be carried out. This results in substantial losses of useful product, additional solvent costs, and the measures which are additionally required when solvents are used in large-scale industrial operation and which relate to operational safety, recovery of the solvent and health and environmental protection.

We have found that methyl m-nitrobenzoate is advantageously obtained from a mixture of methyl m-, p- and o-nitrobenzoate if the isomer mixture is treated with from 10 to 1000% by weight of water in the presence of from 0.05 to 20% by weight of an emulsifier, the percentages being based on the weight of the isomer mixture, (a) in a first stage at from 55° to 100° l C. and a pH from 2 to 8 and then (b) in a second stage at from 10° to 40° C. and a pH of not less than 9.

The nitration can be represented by the following equation:

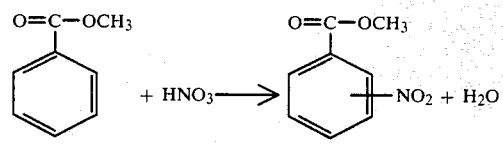

Compared with the conventional processes, the process according to the invention gives methyl m-nitrobenzoate in better yield and purity and by a simpler and more economical route. Organic solvents are not used. With regard to safety in the factory and protection of the operating personnel, the novel process is better and causes less pollution. On the basis of the prior art, all these advantageous results are surprising.

The nitration of methyl benzoate with nitric acid for the preparation of the m-nitro compound can be carried out by a conventional method, for example one of the processes described in the above publications. Nitration is expediently carried out using nitric acid, advantageously concentrated or fuming nitric acid, in the presence of sulfuric acid, advantageously highly concentrated or fuming sulfuric acid. If desired, nitric acid and sulfuric acid can be completely or partly replaced with nitrating acid, ie. a mixture of the two acids. In general, from 85 to 100% strength by weight nitric acid and from 98 to 100% strength by weight sulfuric acid are used. Advantageously, the mixture of nitric acid and sulfuric acid chosen, ie. nitrating acid, contains from 0.2 to 2 moles of nitric acid per mole of sulfuric acid. As a rule, from 2 to 10, preferably from 2 to 3, moles, of nitric acid are used per mole of ester. Instead of nitric acid, it is also possible to use an appropriate amount of a substance which forms this acid in the reaction mixture, for example an inorganic nitrate, such as sodium nitrate or potassium nitrate. If required, urea is used as the nitration catalyst, advantageously in an amount of from 10 to 100, preferably from 45 to 55, % by weight, based on the methyl ester. The reaction is carried out in general at between 0° and +40° C., preferably between 10° and 30° C., under atmospheric or superatmospheric pressure, batchwise or continuously. The solvent medium is in general the acid or the acid mixture itself, if necessary mixed with water in the form of an acid mixture of appropriate concentration.

The reaction can be carried out as follows: a mixture of the starting material and sulfuric acid is brought to the reaction temperature, after which nitric acid, if necessary mixed with sulfuric acid, is slowly added to the stirred mixture, for example in the course of from 15 to 30 minutes. The mixture is kept at the reaction temperature for a further 1-3 hours.

A suitable starting mixture for the novel process is a methyl m-nitrobenzoate which is obtained by one of the conventional working-up procedures. Preferably, however, one of the above nitration processes is carried out, and, after the reaction, the resulting mixture of methyl nitrobenzoate isomers is precipitated from the reaction mixture by dilution with water at from 85° to 100° C., preferably from 95° to 100° C., and is isolated. The precipitation can be carried out under atmospheric or superatomspheric pressure, continuously or batchwise. In general, from 100 to 500, preferably from 100 to 200% by weight, based on the total amount of acid used (calculated as 100%), of water is used. Advantageously, when the reaction is complete the reaction mixture is added directly to the initially taken dilution water at a rate such that the above-mentioned precipitation temperature is established and is maintained during mixing. For the above-mentioned ratio of water to acid, the mixing time is advantageously from 5 to 15 minutes. The diluted mixture is advantageously stirred for a further 10-20 minutes at the precipitation temperature and is then filtered. The filtration residue can then be fed, either directly or advantageously after washing with water, to the treatment according to the invention. The precipitation procedure does not cause any substantial decomposition of the isomer mixture obtained. It can be subjected to purification in the form of the moist filtration residue, without further drying.

Depending on the nitration procedure and the method of working-up, this process gives a mixture which contains from 70 to 94% by weight of the m-ester, from 0.25 to 20% by weight of the o-ester and from 0.25 to 10% by weight of the p-ester and is also contaminated with from 0.1 to 2% by weight of methyl dinitrobenzoate, from 0.1 to 1.5% by weight of nitrophenol compounds and from 0.3 to 2% by weight of other impurities. The isomer mixture is defined here as a mixture of the 3 isomers without the above-mentioned impurities.

The water treatment (purification) is carried out in stage (a) at from 55° to 100° C., advantageously from 60° to 85° C., and in stage (b) at from 10° to 40° C., advantageously from 20° to 30° C., under atmospheric or superatmospheric pressure, continuously or batchwise. As a rule, stage (a) is carried out at above the melting point of methyl m-nitrobenzoate. From 10 to 1000, advantageously from 50 to 200% by weight of water and/or from 0.05 to 20, advantageously from 0.5 to 5, % by weight of an emulsifier, are used, the percentages being based on the weight of the isomer mixture. Expediently, the treatment time in stage (a) is from 0.1 to 10, advantageously from 0.2 to 2, hours, while that in stage (b) is from 0.5 to 25, advantageously from 2 to 5, hours. In stage (a), the pH is brought to 2-8, advantageously 5-7, while in stage (b) the pH is brought to not less than 9, expediently from 9 to 14, advantageously from 10 to 14, in particular from 12 to 13.5.

For the purposes of the present invention, an emulsifier is a substance, or a mixture of substances, which permits or facilitates the formation of an emulsion of methyl o-nitrobenzoate in water. Suitable substances for this purpose are substances as defined in, for example, the chapter on emulsifiers in Ullmanns Enzyklopädie der technischen Chemie (Volume 10, pages 455-464, 4th Edition (1975)). Advantageous substances are non-ionic emulsifiers, such as fatty-acid esters, fatty amines, fatty-acid amides and polyglycol ethers based on polyethylene oxide or polypropylene oxide, preferably of the N 301 to N 318 and N 401 to N 405 types (Ullmann, loc. cit., page 456), in particular of the N 303 and N 304 types, for example those based on fatty acids of 5 to 26 carbon atoms and monohydric or polyhydric alcohols of 1 to 5 carbon atoms, condensed with from 20 to 60 moles of ethylene oxide or propylene oxide; anionic emulsifiers such as salts, expediently alkali metal salts, advantageously sodium and potassium salts, of sulfonic acids, expediently of the A 201 to A 212 types (Ullmann, loc. cit., page 457), advantageously of the A 206 type, in particular esters of sulfosuccinic acid with an alcohol of 1 to 12 carbon atoms; organic phosphoric acid compounds, advantageously of the A 401 to 407 types (Ullmann, loc. cit., page 458), preferably of the A 401 type, in particular esters of phosphoric acid with an alkanol of 1 to 20 carbon atoms or its polyglycol ethers of 20 to 70 carbon atoms; cationic emulsifiers, expediently of the K 101 to 111 types (Ullmann, loc. cit., page 458), advantageously of the K 103 and 104 types, preferably those containing chloride as the anion, in particular with quaternary ammonium cations having 4 alkyl groups of 1 to 20 carbon atoms or 3 alkyl groups of 1 to 20 carbon atoms and a benzyl group as substituents.

The purification can be carried out as follows: Methyl benzoate is nitrated in accordance with one of the above-mentioned procedures, and the reaction mixture is diluted with water and filtered. The still moist filtration residue advantageously contains from 2 to 35% by weight of water. Water and an amount, according to the invention, of an emulsifier are then added to the residue, which is not dried beforehand; the total amount of water is brought to the above amount. It is also possible to add first the emulsifier and then the water to the reaction mixture. Likewise, the emulsifier can be added to the starting mixture before the nitration, or to the reaction mixture during or after the nitration. A suspension is formed, and this is kept first at the higher temperature of stage (a) and then at the lower temperature of stage (b), under the above-mentioned conditions (reaction time, reaction temperature and reaction pH) for the two stages. The methyl m-nitrobenzoate is then isolated in a conventional manner, for example by filtering, washing the residue with water, filtering once again and drying. In general, the resulting methyl m-nitrobenzoate has a purity of 98.9-99.8% by weight; it can contain a residual amount of about 0.05% by weight of methyl p-nitrobenzoate, about 0.1-1% by weight of methyl o-nitrobenzoate and about 0.05% by weight of other impurities. At the end of stage (b), the major part of the o-isomer forms an emulsion with the emulsifier and remains in the filtrate after the methyl m-nitrobenzoate has been isolated. The o-isomer can be isolated from the filtrate by steam distillation. The major part of the p-isomer is hydrolyzed in stage (b), and the resulting p-nitrobenzoic acid is, for example, precipitated at an acidic pH and separated off by filtration. The by-products methyl o-nitrobenzoate and p-nitrobenzoic acid which are separated off can be used for further syntheses.

The methyl m-nitrobenzoate obtainable by the process of the invention is a useful starting material for the preparation of dyes and crop protection agents. Since the resulting methyl m-nitrobenzoate is virtually pure and contains only traces of impurities, this end product is advantageous for direct further processing, for example catalytic reductive alkylation to give methyl m-N,N-dimethylaminobenzoate. Methyl m-N,N-dimethylaminobenzoate can be converted to m-N,N-dimethylaminobenzoic acid, which is an intermediate for the preparation of the dye crystal violet lactone. Regarding the use of these compounds, reference may furthermore be made to the above publications.

EXAMPLES

Example 1

1000 g of water-moist methyl m-nitrobenzoate (containing b 810 g of crude nitro ester and having the composition: 8.8% by weight of o-isomer, 9% by weight of p-isomer, 77.3% by weight of m-isomer and 4.9% by weight of the dinitro compound and other impurities) were suspended in 1000 g of water, and 25 g of an emulsifier prepared by condensation of castor oil with 48 moles of ethylene oxide were added. The suspension was heated at 75° l C., and was brought to pH B 6.3 with NaOH. Thereafter, the mixture was stirred for 30 minutes at 75° C. and then cooled to 22° C. 17 g of NaOH were added, the pH reaching 13. 1 The suspension was stirred for 2.5 hours at 25° C., after which the mixture was filtered under suction, and the residue was washed with water, filtered off under suction and dried to give 590 g of 99.6% pure methyl m-nitrobenzoate of melting point 78° l C. This corresponds to a yield of 93.8% (based on m-nitrobenzoate employed).

Examples 2 To 5

1000 g portions of water-moist methyl 3-nitrobenzoate (containing 950 g of crude nitro ester and having the composition: 10.2% by weight of o-isomer, b 5.2% by weight of p-isomer, 83.4% by weight of m-isomer and 1.2% by weight of other impurities) were purified by the procedure described in Example 1. The amount and chemical description of the emulsifier used in each case, and the yields and purities achieved, are summarized in the Table below:

TABLE

| Example | Emulsifier used | Amount of emulsifier in g | Yield of methyl m-nitrobenzoate | Purity [%] |
|---|---|---|---|---|
| 2 | As for Example 1 | 25 | 95.3% | 99.8 |
| 3 | Sodium salt of di-(2-ethylhexyl) sulfosuccinate | 50 | 96.7% | 99.1 |
| 4 | Dimethylbenzyl-($C_{12}$—$C_{14}$)—alkyl-ammonium chloride | 25 | 98.1% | 99.3 |
| 5 | Acidic ester of phosphoric acid with a $C_{13}$—$C_{15}$—alkanol condensed with 12 moles of ethylene oxide and 6 moles of propylene oxide | 25 | 99.2% | 99.4 |

We claim:

1. A process for the preparation of methyl m-nitrobenzoate from a mixture of methyl m-, p- and o-nitrobenzoate, wherein the isomer mixture is treated with from 10 to 1000% by weight of water in the presence of from 0.05 to 20% by weight of an emulsifier, the percentages being based on the weight of the isomer mixture,
   (a) in a first stage at from 55° to 100° C. and a pH from 2 to 8 and then p1 (b) in a second stage at from 10° to 40° C. and a pH of not less than 9.

2. A process as claimed in claim 1, wherein the treatment is carried out using an isomer mixture from the nitration of methyl benzoate with nitric acid in the presence of sulfuric acid.

3. A process as claimed in claim 1, wherein the treatment is carried out using a mixture which contains from 70 to 94% by weight of the m-ester, from 0.25 to 20% by weight of the o-ester and from 0.25 to 10% by weight of the p-ester and may or may not be further contaminated with from 0.1 to 2% by weight of methyl dinitrobenzoate, from 0.1 to 1.5% by weight of nitrophenol compounds and from 0.3 to 2% by weight of other impurities.

4. A process as claimed in claim 1, wherein the treatment in stage (a) is carried out at from 60° to 85° C.

5. A process as claimed in claim 1, wherein the treatment in stage (b) is carried out at from 20° to 30° C.

6. A process as claimed in claim 1, wherein the treatment is carried out using from 50 to 200% by weight, based on the weight of the isomer mixture, of water.

7. A process as claimed in claim 1, wherein the treatment is carried out using from 0.5 to 5% by weight, based on the weight of the isomer mixture, of an emulsifier.

8. A process as claimed in claim 1, wherein the treatment in stage (a) is carried out for from 0.1 to 10 hours.

9. A process as claimed in claim 1, wherein the treatment in stage (b) is carried out for from 0.5 to 25 hours.

10. A process as claimed in claim 1, wherein the treatment in stage (a) is carried out at a pH of from 5 to 7.

11. A process as claimed in claim 1, wherein the treatment in stage (b) is carried out at a pH of from 9 to 14.

12. A process as claimed in claim 1, wherein the treatment is carried out using a fatty-acid ester, a fatty amine, a fatty-acid amide, a polyglycol ether based on polyethylene oxide or polypropylene oxide, an anionic salt, an organic phosphoric acid compound or a cationic emulsifier.

* * * * *

UNITED STATES PATENT AND TRADEMARK OFFICE
CERTIFICATE OF CORRECTION

PATENT NO. : 4,506,089

DATED : March 19, 1985

INVENTOR(S) : Alfred Hackenberger, Manfred Patsch, Manfred Gaeng

It is certified that error appears in the above-identified patent and that said Letters Patent is hereby corrected as shown below:

In Claim 1, line 9: after "then", cancel "pl".

Signed and Sealed this

Sixteenth Day of July 1985

[SEAL]

Attest:

DONALD J. QUIGG

Attesting Officer

Acting Commissioner of Patents and Trademarks